(12) United States Patent
Reints et al.

(10) Patent No.: US 12,360,637 B2
(45) Date of Patent: Jul. 15, 2025

(54) SYSTEM AND METHOD FOR DETERMINING THE IMPACT OF PERIPHERAL OPTICAL ERRORS ON PATIENT LOCOMOTION

(71) Applicant: AMO Groningen B.V., Groningen (NL)

(72) Inventors: Roy Reints, Meerstad (NL); Marrie van der Mooren, Engelbert (NL); Carmen Canovas Vidal, Groningen (NL); Ariel Zenouda, Herblay-sur-Seine (FR); Yichao Liu, Suresnes (FR); Christopher Reeves, Tuffe val de la Cheronne (FR); Robert Rosen, Groningen (NL)

(73) Assignee: AMO Groningen B.V. (NL)

( * ) Notice: Subject to any disclaimer, the term of this patent is extended or adjusted under 35 U.S.C. 154(b) by 0 days.

(21) Appl. No.: 18/478,835

(22) Filed: Sep. 29, 2023

(65) Prior Publication Data

US 2024/0111383 A1    Apr. 4, 2024

Related U.S. Application Data

(60) Provisional application No. 63/377,700, filed on Sep. 29, 2022.

(51) Int. Cl.
*G06F 3/042* (2006.01)
*G06F 3/01* (2006.01)

(52) U.S. Cl.
CPC ............ *G06F 3/0425* (2013.01); *G06F 3/011* (2013.01)

(58) Field of Classification Search
CPC .................. G06F 3/042–0428; G06F 3/011
See application file for complete search history.

(56) References Cited

U.S. PATENT DOCUMENTS

| 2015/0187224 A1 | 7/2015 | Moncrief et al. |
| 2015/0320547 A1 | 11/2015 | Rosen et al. |

(Continued)

FOREIGN PATENT DOCUMENTS

| EP | 3752045 B1 | 11/2021 |
| JP | 6206949 B2 | 10/2017 |
| WO | 2007048615 A1 | 5/2007 |

OTHER PUBLICATIONS

Liou H.L., et al., "Anatomically Accurate, Finite Model Eye for Optical Modeling," Journal of Optical Society of America, Aug. 1997, vol. 14 (8), pp. 1684-1695.

(Continued)

*Primary Examiner* — Hang Lin

(57) ABSTRACT

A method of quantifying the effect of peripheral optical errors on patient locomotion includes projecting a pattern on the floor that includes a discrete shapes and empty spaces between the discrete shapes. The method also includes tracking a position of the participant along the pattern as the participant traverses the pattern, and determining foot placement accuracy, utilizing a optical motion capture system and a computer, as the participant walked through the pattern by determining a total area of overlap between the participant's feet and the empty spaces of the pattern. In another embodiment, the method includes arranging obstacles in front of a participant, intermittently displaying a character in front of the participant, determining participant's accuracy in identifying or counting the characters, and determining the participant's step length and foot clearance as the participant steps over the obstacles to quantify the effect of the peripheral optical errors on the participant's locomotion.

18 Claims, 7 Drawing Sheets

(56) References Cited

U.S. PATENT DOCUMENTS

| | | | |
|---|---|---|---|
| 2017/0258578 A1 | 9/2017 | Rosen et al. | |
| 2017/0273552 A1* | 9/2017 | Leung | A61B 3/005 |
| 2021/0045628 A1* | 2/2021 | Bennett | A61B 3/0041 |
| 2022/0392370 A1* | 12/2022 | Kweon | A61H 3/00 |
| 2024/0109543 A1 | 4/2024 | Reints et al. | |
| 2024/0374375 A1 | 11/2024 | Romashchenko et al. | |

OTHER PUBLICATIONS

Gomaa A., et al., "Studying Person-Specific Pointing and Gaze Behavior for Multimodal Referencing of Outside Objects from a Moving Vehicle," ICMI '20: Proceedings of the 2020 International Conference on Multimodal Interaction, Oct. 2020, pp. 501-509, XP058483095, DOI: 10.1145/3382507.3418817 ISBN: 978-1-4503-7581-8.

Graci V., et al., "Peripheral Visual Cues Affect Minimum-foot-clearance During Overground Locomotion," Gait & Posture, Oct. 2009, vol. 30(3), pp. 370-374. XP026467570, ISSN: 0966-6362, DOI: 10.1016/j.gaitpost.2009.06.011.

Jansen S.E.M., et al., "Human Locomotion Through a Multiple Obstacle Environment: Strategy Changes as a Result of Visual Field Limitation," Experimental Brain Research, Jul. 2011, vol. 212(3), pp. 449-456. XP019924746, ISSN: 1432-11 06, DOI: 10.1007/S00221-011-2757-1.

Knopf N.A., et al., "Initial Mobility Behaviors of People With Visual Impairment in a Virtual Environment Using a Mixed Methods Design," 2017 IEEE Life Sciences Conference (LSC), Dec. 2017, pp. 153-156, XP033307043, DOI: 10.1109/LSC.2017.8268166.

Miyasike-Dasilva V., et al., "A Role for the Lower Visual Field Information in Stair Climbing," Gait & Posture, May 2019, vol. 70, pp. 162-167, XP085662176, ISSN: 0966-6362, DOI: 10.1016/j.gaitpost.2019.02.033.

Atchison, David A, "Optical Models for Human Myopic Eyes", Vision Research, vol. 46, pp. 2236-2250, 2006.

ISO 11979-1, "Part 1—Vocabulary", Ophthalmic Implants—Intraocular Lenses, Edition 4, 16 pages, Nov. 2018.

ISO 11979-2, "Part 2—Optical Properties and Test Methods", Opthalmic Implants—Intraocular Lenses, Edition 2, 30 pages, Aug. 15, 2014.

* cited by examiner

SYSTEM AND METHOD FOR DETERMINING THE IMPACT OF PERIPHERAL OPTICAL ERRORS ON PATIENT LOCOMOTION

CROSS-REFERENCE TO RELATED PATENT APPLICATIONS

This application claims priority to U.S. Provisional Application No. 63/377,700, filed on Sep. 29, 2022, which is hereby incorporated by reference in its entirety.

BACKGROUND

Field

The present disclosure relates to various systems and methods for determining the impact of peripheral optical errors on patient locomotion.

Description of the Related Art

Peripheral vision plays a crucial role in mobility. When peripheral vision is reduced, mobility can be negatively affected. For instance, peripheral optical errors may cause an individual to not notice obstacles in the individual's periphery and may thus adversely impact locomotion.

SUMMARY

The present disclosure relates to various systems and methods for determining the impact of peripheral optical errors or aberrations on a patient's locomotion. In one embodiment, the method includes projecting, from an overhead video projector, a pattern on a floor in front of a participant. The pattern includes a number of discrete shapes and a number of empty spaces between the number of discrete shapes. The method also includes tracking, with an optical motion capture system, a position of the participant along the pattern as the participant traverses the pattern, and determining foot placement accuracy, utilizing the optical motion capture system and a computer, as the participant walked through the pattern by determining a total area of overlap between the participant's feet and the number of empty spaces of the pattern. The method also includes quantifying the effect of the peripheral optical errors on the patient's locomotion based on the foot placement accuracy.

In another embodiment, the method includes arranging, on a floor, a number of obstacles in front of a participant. The method also includes intermittently displaying, on a display centered in front of the participant, at least one character, and determining an accuracy of the participant to correctly identify or count each of the at least one character intermittently displayed on the display as the participant traverses the number of obstacles. The method further includes tracking, with an optical motion capture system, a position of the participant as the participant traverses the number of obstacles, and determining, with the optical motion capture system and a computer, a clearance between each of the number of obstacles and a foot of the participant as the participant stepped over the number of obstacles and a step length of the participant as the participant stepped over the number of obstacles. The method also includes quantifying the effect of the peripheral optical errors on the participant's locomotion based on an increase in at least one of the clearance and the step length.

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter. One or more of the described features or tasks may be combined with one or more other described features or tasks to provide a workable system, device, or method.

BRIEF DESCRIPTION OF THE DRAWINGS

The accompanying drawings, together with the specification, illustrate exemplary embodiments of the present disclosure, and, together with the description, serve to explain the principles of the present disclosure. The drawings are not necessarily drawn to scale.

DETAILED DESCRIPTION

The present disclosure relates to various systems and methods for determining the impact of peripheral optical errors (aberrations) on patient locomotion or mobility (e.g., walking or other real-life tasks). The peripheral optical errors may be caused, for example, by the individual's natural lenses, contact lenses, or intraocular lenses (IOLs). The systems and methods of the present disclosure are configured to isolate the performance of the individual's peripheral vision from the performance of the individual's central vision to determine the effect of the peripheral optical errors on the participant's locomotion. For instance, in one or more embodiments, the systems and methods of the present disclosure are configured to generate a first task to occupy the participant's central vision during the performance of a second task that occupies the subject's peripheral vision. The impact of the peripheral optical errors may then be utilized to develop glasses, contact lenses, or IOLs for the individual that reduce the effect of the peripheral optical errors on the individual's locomotion. Additionally, in one or more embodiments in which the individual already has IOLs, the impact of the peripheral optical errors determined according to the systems and methods of the present disclosure may be utilized to modify or redesign the IOL or to select a piggyback IOL having a different configuration to reduce the impact of the peripheral optical errors on the individual's locomotion.

Figure 1:
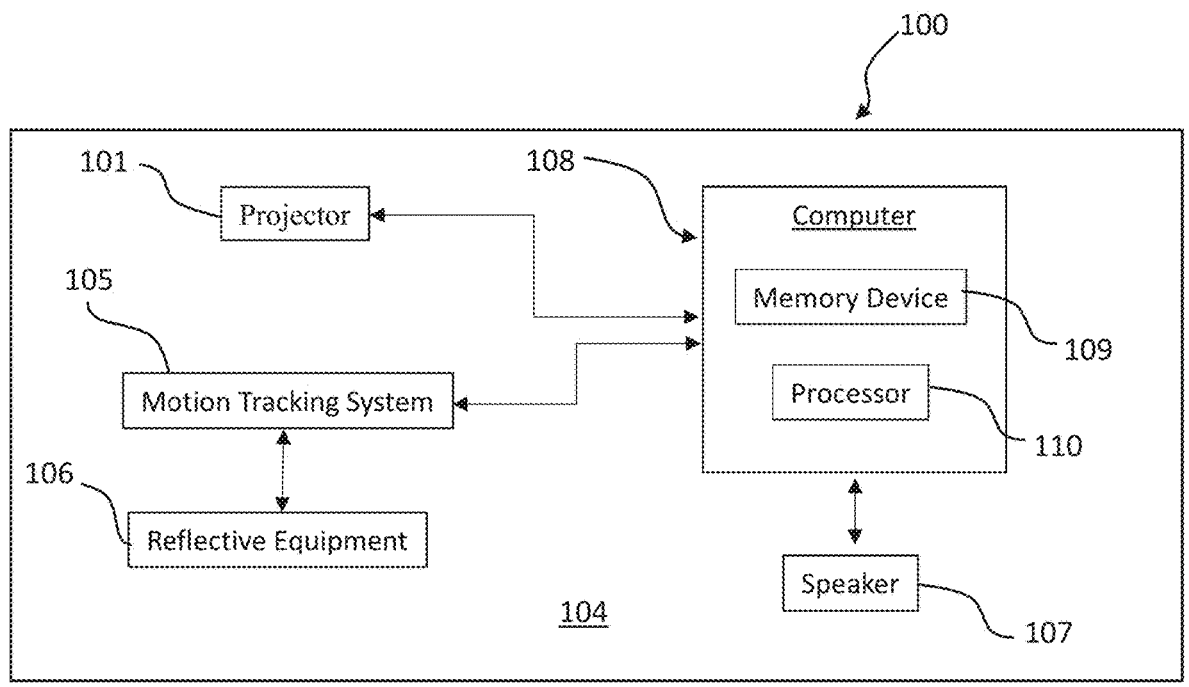
FIG. 1 is a system according to one embodiment of the present disclosure for determining the impact of peripheral optical errors on patient locomotion, the system including an overhead video projector, optical motion capture system, a speaker, and a computer.
Figure 3:
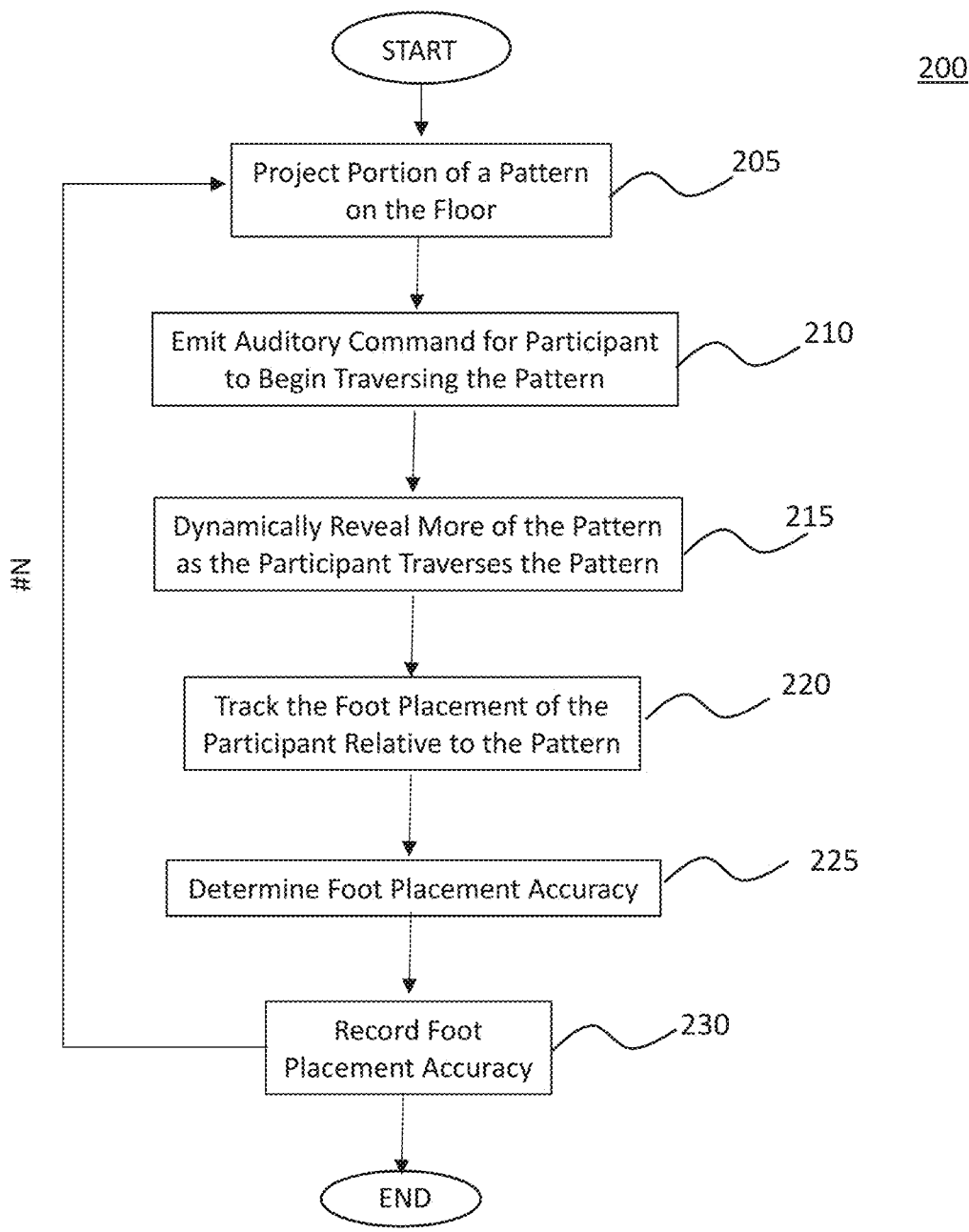
FIG. 3 is a flowchart illustrating tasks of a method of determining the impact of peripheral optical errors on patient locomotion according to one embodiment of the present disclosure utilizing the system of FIG. 1.

FIG. 1 depicts a system 100 according to one embodiment of the present disclosure for determining the impact of peripheral optical errors (e.g., peripheral optical errors in an individual's natural lens, contact lens, or an IOL) on patient locomotion, and FIG. 3 depicts a flowchart illustrating tasks of a method 200 of determining the impact of peripheral optical errors on patient locomotion according to one embodiment of the present disclosure utilizing the system 100 of FIG. 1.

Figure 2A:
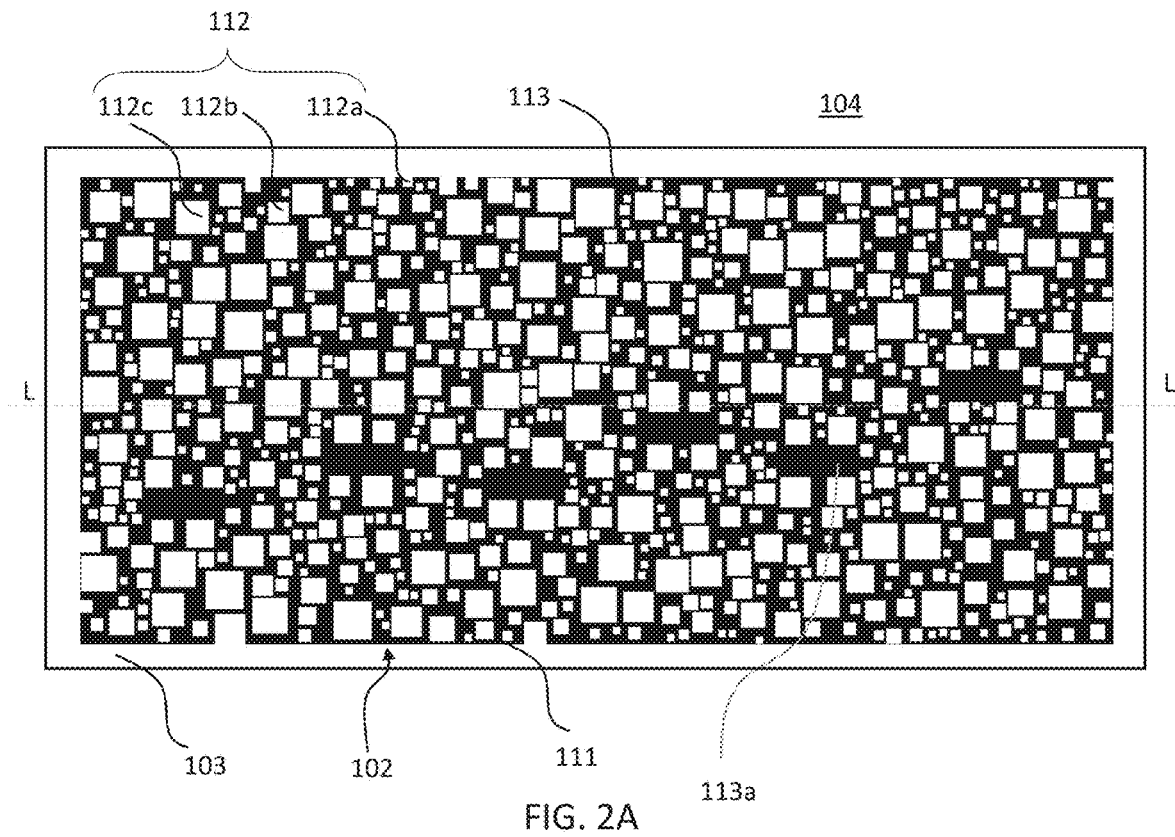
FIG. 2A depicts a pattern projected by the overhead projector of the system of claim 1.
Figure 2B:
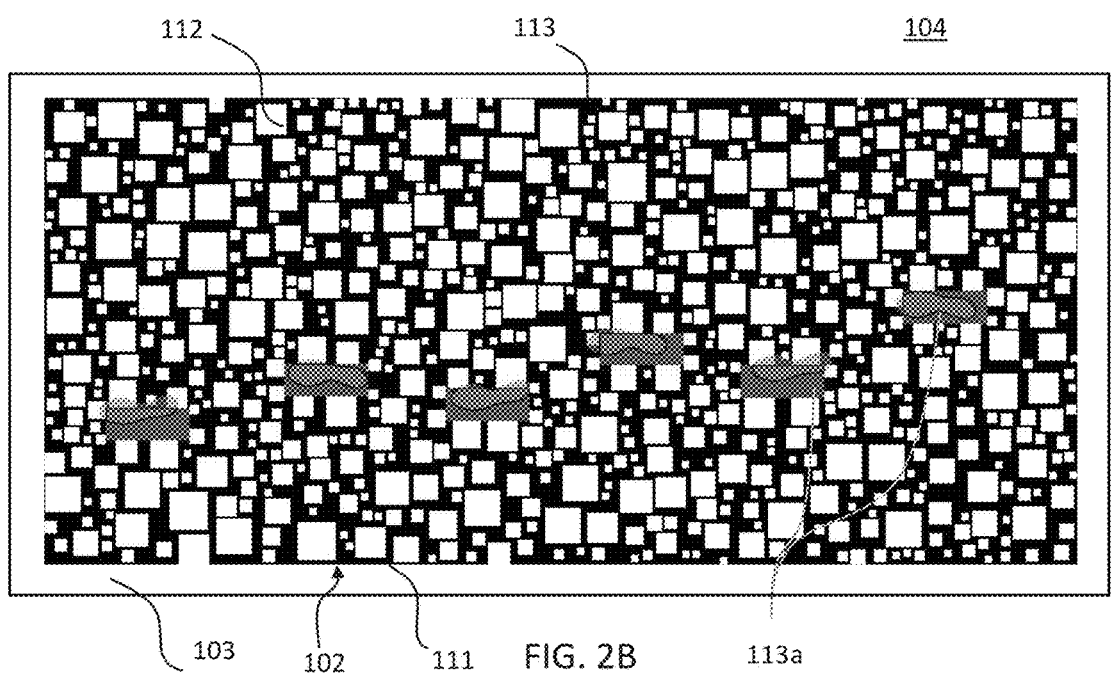
FIG. 2B depicts the pattern projected by the overhead projector and the participant's foot placement overlaid on pattern.

In the embodiment illustrated in FIGS. 1-2B, the system 100 includes a video projector 101 configured to project a pattern 102 on the floor 103 of a room 104, a motion tracking system 105 (e.g., an optical motion capture system) configured to determine (e.g., measure or calculate) the position of the patient's head, torso, pelvis, and foot placement during the test, reflective equipment 106 (e.g., a reflective hat, jacket, and shoes, equipped with reflective markers) on the patient to enable the motion tracking system 105 to track the position of the patient's head, torso, pelvis, and foot placement during the test, a speaker 107 configured to emit audio instructions to the participant, and a computer 108 (e.g., a laptop, a desktop, or a tablet computer) connected to (in electronic communication with) the overhead video projector 101, the motion tracking system 105, and the speaker 107. The video projector 101, the motion tracking system 105, the speaker 107, and the computer 108 may be any suitable commercial off-the-shelf components or they may be custom-designed components.

As described in more detail below, the pattern 102 projected by the overhead video projector 101 is configured to simulate a complex terrain (e.g., a cobblestone pathway) that the participant must traverse, and the pattern 102 is dynamically revealed in front of the participant as the participant traverses the pattern. In general, when people are walking, their central vision is focused on a point or region that is approximately two stride lengths ahead of the individual's current position. Accordingly, in one or more embodiments, the pattern 102 may be revealed only two stride lengths ahead of the participant such that the pattern 102 is not visible (or is substantially not visible) in the participant's central vision. Accordingly, as the participant traverses the pattern 102, the participant must rely solely (or substantially solely) on his or peripheral vision for foot placement whilst using their central vision to predict future pattern navigation 102. That is, dynamically revealing the pattern 102 in front of the individual as he or she traverses the pattern 102 prevents (or at least mitigates against) the participant utilizing his or her central vision to aid him or her in traversing the pattern 102 such that the accuracy of the participant's foot placement while traversing the pattern 102 is indicative of the effects of the peripheral optical errors in the participant's vision (i.e., dynamically revealing the pattern 102 isolates the effects of the peripheral optical errors (aberrations) on the participant's locomotion).

In one or more embodiments, the computer 108 includes a non-volatile memory device 109 having instructions (e.g., computer-readable code) stored therein, and a processor 110 coupled to the non-volatile memory device 109. As described in more detail below, the instructions stored in the non-volatile memory device 109, when executed by the processor 110, cause the processor 110 to determine (e.g., calculate or compute) the foot placement accuracy of the participant as the participant traverses the pattern 102.

The term "processor" is used herein to include any combination of hardware, firmware, and software, employed to process data or digital signals. The hardware of a processor may include, for example, application specific integrated circuits (ASICs), general purpose or special purpose central processors (CPUs), digital signal processors (DSPs), graphics processors (GPUs), and programmable logic devices such as field programmable gate arrays (FPGAs). In a processor, as used herein, each function is performed either by hardware configured, i.e., hard-wired, to perform that function, or by more general purpose hardware, such as a CPU, configured to execute instructions stored in a non-transitory storage medium. A processor may be fabricated on a single printed wiring board (PWB) or distributed over several interconnected PWBs. A processor may contain other processors; for example, a processor may include two processors, an FPGA and a CPU, interconnected on a PWB.

In one or more embodiments, the system 100 may also include a black carpet or mat 111 on the floor 103 to reduce floor-based light reflections from overhead lights in the room 104 and to increase the contrast of the pattern 102 projected on the black carpet or mat 111 by the overhead projector 101. Additionally, in one or more embodiments, the overhead lights have a lighting level of approximately 14.3 lux, which provides some ambient light and allows lower contrast levels projected from the overhead video projector 101 to be visible on the floor 103 or the black carpet or mat 111. In one or more embodiments, the contrast of the pattern 102 and/or the illumination of the overhead lights (i.e., the ambient lighting) in the room 104 may be adjusted or varied during the performance of a test utilizing the system 100.

The pattern 102 projected on the floor 103 or the black carpet or mat 111 on the floor 103 includes a series of discrete, randomly distributed geometric shapes (e.g., squares) separated from each other by a series of empty spaces. In the embodiment illustrated in FIG. 2A, the pattern 102 includes a series of randomly distributed squares 112 that are separated from each other by empty spaces 113 (i.e., places in which the floor 103 or the black carpet or mat 111 is not illuminated by the overhead video projector 101). The size and arrangement of the squares 112 and the size and arrangement of the empty spaces 113 between the squares 112 are selected such at least some of the empty spaces 113 are sufficiently large such that a foot or shoe of the participant can fit within those empty spaces 113. In one or more embodiments, these larger portions 113a of the empty spaces 113 have a length and a width that is 1 cm (or approximately 1 cm) larger than the shoe size of the participant such that 1 cm (or approximately 1 cm) margin extends around the participant's shoe when the participant's shoe is centered the larger portions 113a of the empty spaces 113. Additionally, in the illustrated embodiment, these larger portions 113a of the empty spaces 113 are arranged along a direction of a longitudinal centerline L of the pattern 102 or may deviate slightly to the left or the right over the length of the pattern. Alternatively, they may be offset to the left and/or the right of the longitudinal centerline L of the pattern 102 (i.e., the larger portions 113a are successively arranged further along the longitudinal centerline L and the larger portions 113a of the empty spaces 113 alternately deviate to the left and the right of the longitudinal centerline L). In one or more embodiments, the squares 112 may each have a length and a width in a range from approximately 12 cm to approximately 18 cm. In the illustrated embodiment, the squares 112 each have a size of approximately 15 cm×approximately 15 cm. In one or more embodiments, the squares 112 may include a plurality of different sizes of squares. For example, in one or more embodiments, the squares 112 may include a plurality of relatively small squares 112*a*, a plurality of medium-sized squares 112*b*, and a plurality of relatively large squares 112*c*. In one or more embodiments, the relatively large squares 112*a* may have a length and a width in a range from approximately 8 cm to approximately 15 cm, the medium squares 112*b* may have a length and a width in a range from approximately 5 cm to approximately 8 cm, and the relatively smaller squares 112*a* may have a length and a width in a range from approximately 3 cm to approximately 4 cm. Additionally, in one or more embodiments, the overall size of the pattern 102 may have a length in a range from approximately 3 meters to approximately 5 meters, and a width in a range from approximately 1 meter to approximately 3 meters. In one embodiment, the overall size of the pattern 102 has length of approximately 4.06 meters, and a width of approximately 1.83 meters. In one or more embodiments, the squares 112 of the pattern 102 may have any other suitable size depending, for instance, on the size of the participant's feet or shoes, the walking speed of the participant, and/or the stride length of the participant. FIG. 2B depicts the foot placement of a participant as the participant traversed the pattern 102. As shown in FIG. 2B, the areas of overlap between the participant's feet and the squares 112 of the pattern 102 are shown lighter than the areas of overlap between the participant's feet (or shoes) and the empty spaces 113.

Additionally, in one or more embodiments, the pattern 102 may be adjusted based on the participant's gait, such as the stride length of the participant at the participant's natural or preferred walking speed. For example, in one or more embodiments, the longitudinal length between adjacent larger portions 113*a* of the empty spaces 113 may be increased with increasing stride length of the participant. In one or more embodiments the longitudinal length between adjacent larger portions 113*a* of the empty spaces 113 may be in a range from approximately 0.45 meters (m) to approximately 0.8 m (e.g., approximately 0.45 m, approximately 0.5 m, approximately 0.55 m, approximately 0.6 m, approximately 0.65 m, approximately 0.7 m, approximately 0.75 m, or approximately 0.8 m). In one or more embodiments, the longitudinal length (delta_L) between adjacent larger portions 113*a* of the empty spaces 113 may be calculated as follows: delta_L=(1-ratio_vari_L)*median, where the ratio_vari_L is the variation in the participant's step length and median is the median step length of the participant. For instance, in one or more embodiments, the ratio_vari_L may be 0.15 and the median may be determined from the following list, 0.8 m, 0.75 m, 0.7 m, 0.6 m, 0.55 m, 0.5 m, or 0.45 m. Additionally, in one or more embodiments, the pattern 102 may be adjusted depending on whether the participant is intended to start traversing the pattern 102 with the participant's left foot or right foot. FIG. 2A depicts an embodiment of the pattern 102 in which the participant has a stride length of approximately 0.70 m and the participant is intended to traverse pattern 102 from right to left, starting with the participant's right foot.

Additionally, in the illustrated embodiment, the system 100 is configured to dynamically reveal the pattern 102 as the participant traverses across the pattern 102. In one or more embodiments, the system 100 is configured to reveal the portion of the pattern 102 that is two steps (or approximately two steps) ahead of the participant (e.g., the length of the pattern 102 revealed in front of the participant is equal or substantially equal to two stride lengths of the participant at the participant's walking speed). For instance, in one or more embodiments, the optical motion capture system 105 is configured to capture the position of the participant along the length of the pattern 102 and to transmit this position to the computer 108. In response, the instructions stored in the non-volatile memory device 109, when executed by the processor 110, cause the computer 108 to determine (e.g., calculate or compute) the location of the pattern 102 that would extend two stride lengths (or approximately two stride lengths) in front of the participant, and transmits a signal to the overhead video projector 101 such that the overhead video projector 101 reveals a portion of the pattern 102 in front of the participant that is equal or substantially equal in length to two stride lengths (or approximately two stride lengths) of the participant moving at the participant's preferred or natural walking speed. Dynamically revealing the pattern 102 ahead of the participant as the participant traverses the pattern 102 requires the participant to utilize his or her peripheral vision to properly place his/her feet inside the larger portions 113*a* of the empty spaces 113. Otherwise, initially revealing the entire pattern 102 would enable the participant to utilize his or her central vision prior to the beginning of the test (and during the test) to determine the proper foot placement along the pattern 102, and thus the foot placement accuracy would not accurately indicate the effect of the peripheral optical errors on the participant's locomotion.

In one or more embodiments, the computer 108 is configured to control the overhead video projector 101 to adjust the contrast of the pattern 102 projected by the overhead video projector 101. For instance, in one or more embodiments, the computer 108 is configured to adjust the pattern 102 between a low contrast setting (e.g., 4.1%), a medium contrast setting (e.g., 6.19%), and a high contrast setting (e.g., 9.36%). Additionally, in one or more embodiments, ambient lighting conditions in the room 104 may be adjusted using, for example, 9 LED panels (e.g., the ambient lighting conditions in the room 104 may be adjusted between a bright lighting condition and a low (or dim) lighting condition).

As described in more detail below, the configuration of the pattern 102 (e.g., the arrangement of the squares 112 and the empty spaces 113, and/or the contrast of the squares 112 on the floor 103 or the black carpet or mat 111) may be varied (e.g., randomized or pseudo-randomized) between subsequent tests to prevent the participant from memorizing the course.

FIG. 3 depicts a flowchart illustrating tasks of a method 200 for determining the impact of peripheral optical errors on patient locomotion according to one embodiment of the present disclosure. In the illustrated embodiment, the method 200 includes a task 205 of projecting, from the overhead video projector 101, a portion of the pattern 102 on the floor 103 or the black carpet or mat 111 on the floor 103 in front of a participant wearing the reflective equipment 106 (e.g., a reflective hat, jacket, and shoes, equipped with reflective markers). As described above, the configuration of the pattern may be based on the participant's walking speed, natural gait (stride length), and/or shoe size. In one or more embodiments, a baseline test of the participant's walk without the pattern projected on the floor may be performed to determine the participant's natural stride and walking speed.

In the illustrated embodiment, the method 200 also includes a task 210 of emitting an auditory command or instruction from the speaker 107 for the participant to begin traversing the pattern 102 projected in task 205.

In the illustrated embodiment, the method 200 also includes a task 215 of dynamically revealing more of the pattern 102 in front of the participant as the participant traverses the pattern 102. In one or more embodiments, the task 215 may include dynamically revealing the pattern 102 such that the pattern 102 extends two steps (or approximately two steps) ahead of the position of the participant, as determined by the motion tracking system 105, based on the participant's gait, such as the participant's stride length and/or the walking speed of the participant. In one or more embodiments, the task 215 includes tracking, with the motion tracking system 105, a position of the participant (e.g., a position of the participant's head) on the floor 103 or the black mat 111, determining (e.g., calculating or measuring), with the computer 108, a length of the pattern 102 to reveal in front of the participant that corresponds to two steps (or approximately two steps) ahead of the participant based on the participant's gait (e.g., stride length and walking speed), and transmitting a command to the projector to reveal the determined length of the pattern 102 in front of the participant.

In the illustrated embodiment, the method 200 also includes a task 220 of tracking, with the motion tracking system 105, the foot placement of the participant relative to the larger portions 113a of the empty spaces 113 between the squares 112 of the pattern 102 as the participant traverses the pattern 102. In one or more embodiments, the task 220 may include tracking, with the motion tracking system 105, the foot placement of the participant relative to the squares 112 of the pattern 102 as the participant traverses the pattern 102.

In the illustrated embodiment, the method 200 also includes a task 225 of determining (e.g., calculating or measuring), with the computer 108, the foot placement accuracy (e.g., the extent of the misstep errors) of the participant as the participant traverses the pattern 102. For example, in one or more embodiments, the task 225 includes determining (e.g., measuring or calculating), by the computer 108, the area of overlap between the participant's feet (or shoes) and the larger portions 113a of the empty spaces 113 (e.g., number of pixels of the larger portions 113a of the empty spaces 113 that overlap with the participant's foot with each step), as shown in FIG. 2B. In one or more embodiments, the task 225 may include determining (e.g., measuring or calculating), by the computer 108, the area of overlap between the participant's feet (or shoes) and the squares 112 (e.g., number of pixels of the squares 112 that overlap with the participant's foot with each step). In one or more embodiments, the task 220 may include determining (e.g., measuring or calculating), by the computer 108, a ratio of the area of overlap between the participant's feet (or shoes) and the larger portions 113a of the empty spaces 113 to the total area of the larger portions 113a and/or the total area of the empty spaces 113. In one or more embodiments, the task 220 may include determining (e.g., measuring or calculating), by the computer 108, a ratio of the area of overlap between the participant's feet (or shoes) and the squares 112 to the total area of the squares 112. In one or more embodiments, the task 220 may include determining (e.g., measuring or calculating), by the computer 108, a ratio of the area of overlap between the participant's feet (or shoes) and the squares 112 to the area of overlap between the participant's feet (or shoes) and the empty spaces 113 (e.g., the larger portions 113a).

In the illustrated embodiment, the method 200 includes a task 230 of recording, in the memory device 109 of the computer 108, the foot placement accuracy result determined in task 225. In general, the worse the foot placement accuracy of the participant (e.g., the greater the overlap between the participant's feet or shoes and the squares 112 of the pattern 102), the greater the extent of the impact of the peripheral optical errors on the participant's mobility (locomotion).

The tasks 205-230 may be repeatedly performed N times (where N is an integer) and one or more characteristics of the pattern 102 may be varied between subsequent repetitions of tasks 205-230, such as the arrangement of the squares 112 of the pattern 102, the locations of the larger portions 113a of the empty spaces 113, the contrast of the squares 112 of the pattern 102, and/or the ambient lighting conditions in the room 104. In one or more embodiments, the method 200 may also include a task of emitting an auditory alert (e.g., a beep) from the speaker 107 when the participant has completed traversing through the pattern 102 to signal to the participant to return to the start of the pattern 102 to repeat the test.

Figure 4A:
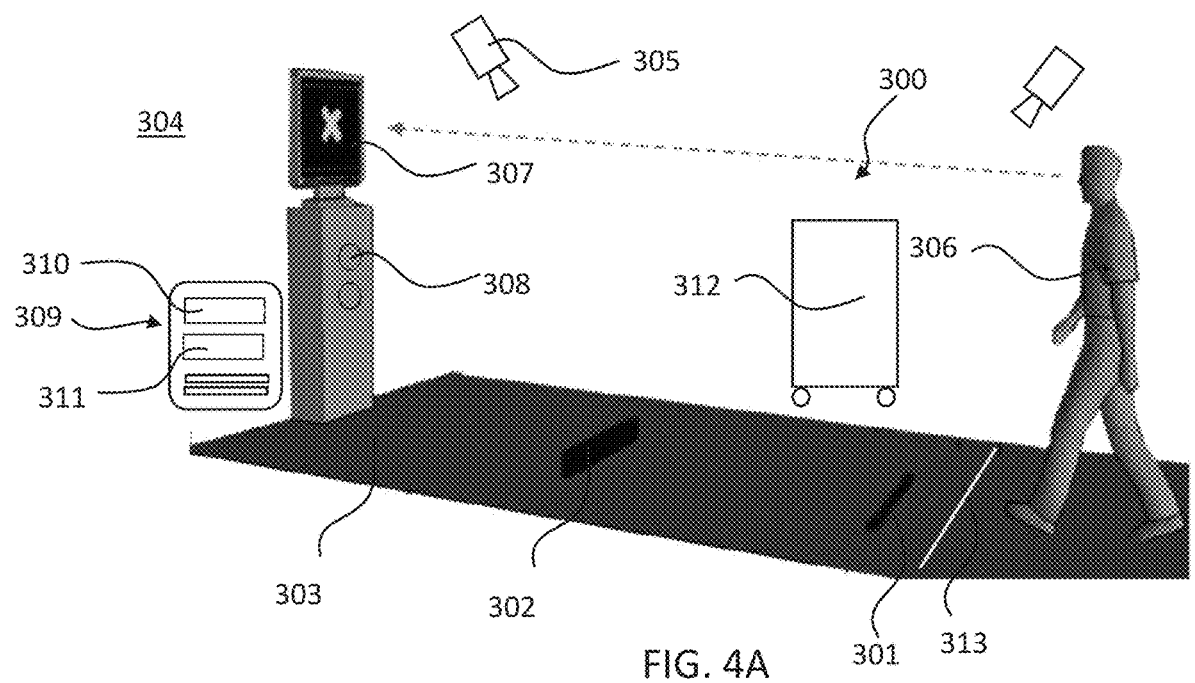
FIGS. 4A-4B depict a system according to another embodiment of the present disclosure for determining the impact of peripheral optical errors on patient locomotion, the system including obstacles, an optical motion capture system, a display, a speaker, and a computer.
Figure 4B:
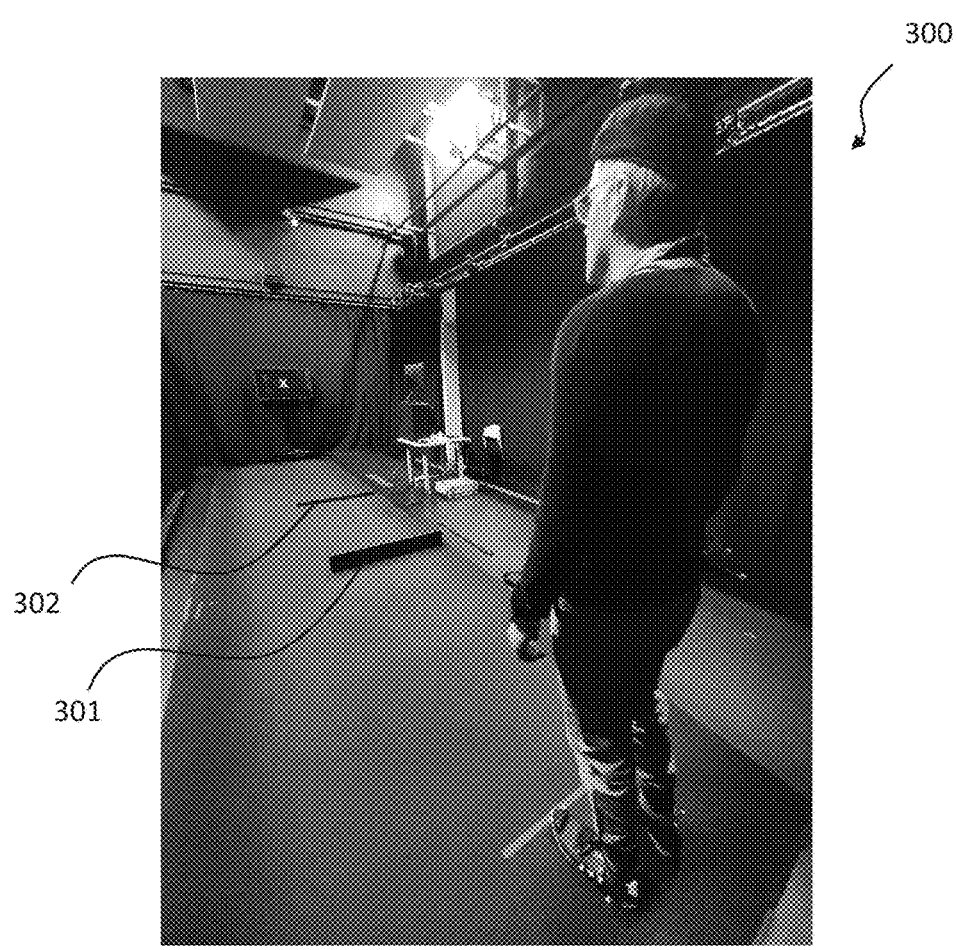
Figure 5:
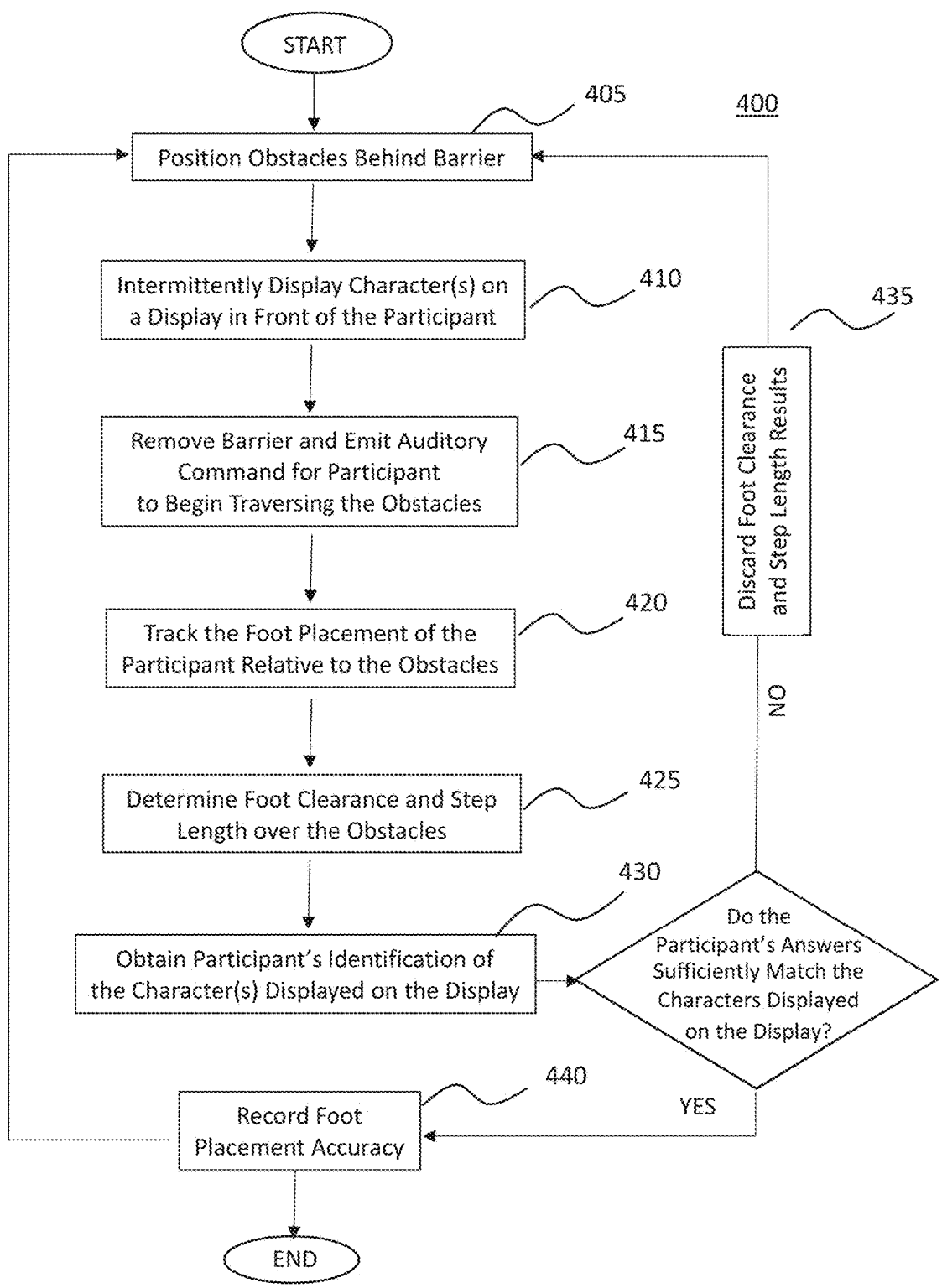
FIG. 5 is a flowchart illustrating tasks of a method of determining the impact of peripheral optical errors on patient locomotion according to one embodiment of the present disclosure utilizing the system of FIGS. 4A-4B.

FIGS. 4A-4B depict a system 300 according to another embodiment of the present disclosure for determining the impact of peripheral optical errors (e.g., peripheral optical errors in an individual's natural lens, contact lens, or an IOL) on patient locomotion, and FIG. 5 depicts a flowchart illustrating tasks of a method 400 of determining the impact of peripheral optical errors on patient locomotion according to one embodiment of the present disclosure utilizing the system 300 of FIGS. 4A-4B.

In the embodiment illustrated in FIGS. 4A-4B, the system 300 includes a plurality of obstacles (e.g., a first obstacle 301 and a second obstacle 302) on the floor 303 of a room 304, an optical motion capture system 305 configured to determine (e.g., measure or calculate) the position of the participant's head, torso, pelvis, and foot placement during the test, reflective equipment 106 (e.g., a reflective hat, jacket, and shoes, equipped with reflective markers) on the participant to enable the optical motion capture system 305 to track the position of the patient's head, torso, pelvis, and foot placement during the test, a display 307 (e.g., a television screen or a monitor) at one end of the room 304 at eye-level (or approximately eye-level) with the participant that is configured to display random characters (e.g., letters in a random order) during the test, a speaker 308 configured to emit audio instructions to the participant, and a computer 309 (e.g., a laptop, a desktop, or a tablet computer) connected to (in electronic communication with) the optical motion capture system 305, the display 307, and the speaker 308.

In one or more embodiments, the computer 309 includes a non-volatile memory device 310 having instructions (e.g., computer-readable code) stored therein, and a processor 311 coupled to the non-volatile memory device 310. As described in more detail below, the instructions stored in the non-volatile memory device 310, when executed by the processor 311, cause the display 307 to intermittently display character(s) and cause the processor 311 to determine (e.g., calculate or compute) the placement and clearance of the participant's feet relative to the first and second obstacles 301, 302.

Additionally, in the illustrated embodiment, the system 300 includes a movable barrier 312 (e.g., a wall panel on wheels) that is configured to conceal the first and second obstacles 301, 302 from the view of the participant but reveal the display 307 prior to the start of the test.

As described in more detail below, the first and second obstacles 301, 302 are configured to simulate a complex terrain (e.g., rocks or other objects on a pathway) that the participant must traverse, and the display 307 is configured to occupy the participant's central vision during traversal of the first and second obstacles 301, 302. The correct identification of the character(s) displayed on the display 307 in front of the participant requires use of the participant's central vision, and the proper placement of the participant's feet with respect to the obstacles 301, 302 requires use of the participant's peripheral vision. In this manner, the simultaneous or substantially simultaneous display of the one or more characters on the display 307 while the participant is traversing the obstacles 301, 302 is configured to occupy the participant's central vision during traversal of the obstacles 301, 302, which prevents (or at least mitigates against) the participant utilizing his or her central vision to aid him or her in traversing the obstacles 301, 302 such that the accuracy of the participant's foot placement while traversing the obstacles 301, 302 is indicative of the effects of the peripheral optical errors. That is, the system 300 requires the participant to perform dual-tasks simultaneously (or substantially simultaneously), with one task requiring the participant's central vision to perform and the other task requiring the participant's peripheral vision to perform, which isolates the effects of the peripheral optical errors (aberrations) on the participant's peripheral vision such that the accuracy of the participant's foot placement (e.g., the participant's step length while stepping over the first and second obstacles 301, 302 and the participant's toe clearance while stepping over the first and second obstacles 301, 302) while traversing the first and second obstacles 301, 302 is indicative of the effects of the peripheral optical errors. In general, a greater toe clearance between the participant's foot and the first and second obstacles 301, 302 and a greater step length while stepping over the first and second obstacles 301, 302 are indicative of cautious walking behavior and therefore greater impairment due to the peripheral optical errors in the participant's vision (i.e., greater toe clearance and greater step length indicate participant's uncertainty in the placement and height of the first and second obstacles 301, 302 and thus greater impairment due to the peripheral optical errors in the participant's vision).

In one or more embodiments, each of the first and second obstacles 301, 302 may have a height in a range from approximately 5 cm to approximately 15 cm. Additionally, in one or more embodiments, each of the first and second obstacles 301, 302 may have a width in a range from approximately 0.75 m to approximately 1.25 m (e.g., approximately 1 m). In one or more embodiments, the first obstacle 301 may be spaced approximately 2.1 m, or approximately 2.3 m, or approximately 2.5 m from a starting line 313. In one or more embodiments, the second obstacle 302 may be spaced approximately 4.4 m, or approximately 4.6 m, or approximately 4.8 m from the starting line 313. As described in more detail below, the heights of the first and second obstacles 301, 302 and/or the positions of the first and second obstacles 301, 302 from the starting line 313 may be varied (e.g., randomized) between subsequent tests to prevent the participant from memorizing the course.

With reference now to FIG. 5, the method 400 includes a task 405 of positioning the first and second obstacles 301, 302 behind the movable barrier 312 in front of a participant wearing the reflective equipment 106 (e.g., a reflective hat, jacket, and shoes, equipped with reflective markers).

Figure 6:
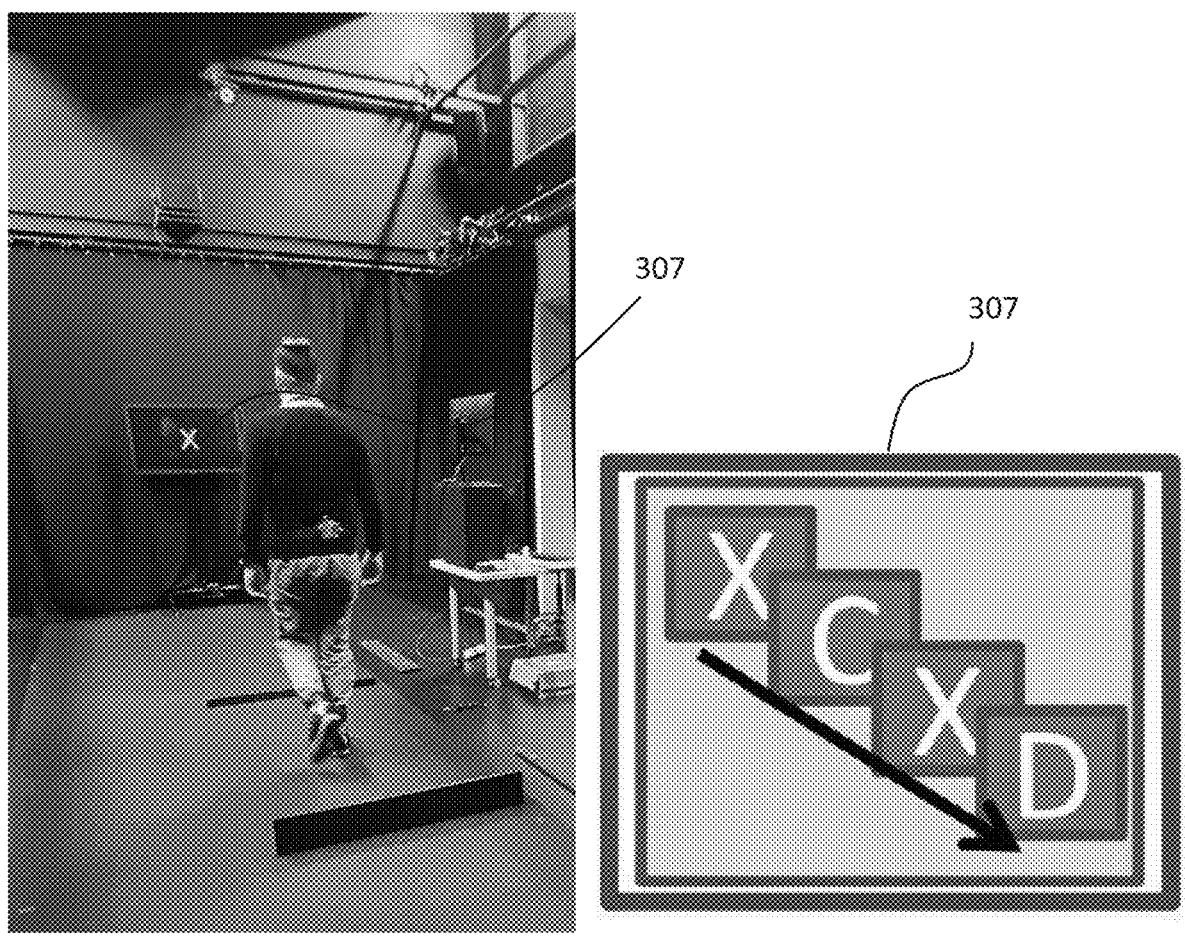
FIG. 6 depicts the display of the embodiment of the system depicted in FIGS. 4A-4B.

In the illustrated embodiment, the method 400 also includes a task 410 of periodically or randomly displaying characters (e.g., numeric, alphabetic, alphanumeric, or symbols) (i.e., an optotype) on the display 307 in front of the participant as the participant traverses the first and second obstacles 301, 302 positioned in task 405. In one or more embodiments, the task 410 of displaying the characters on the display 307 may begin before the participant begins traversing the first and second obstacles 301, 302 so that participant's central vision is focused on the display 307 throughout the test. In one or more embodiments, the characters displayed in task 415 have a size corresponding to 2-degrees (or approximately 2-degrees) of the participant's visual angle, and the size of the characters is reduced as the participant walks forward toward the display 307 such that characters continue to occupy 2-degrees (or substantially 2-degrees) of the participant's visual angle (i.e., the participant's visual angle occupied by the characters displayed on the display 307 remains constant (or substantially constant)). Reducing the size of the characters as the participants moves toward the display 307 such that the characters always occupy 2-degrees (or approximately 2-degrees) of the participant's visual angle reduces the participant's ability to see the characters on the display 307 if they were to look down while stepping over the obstacles 301, 302. That is, in task 410, the optotype size reduces with the participant's advancement toward the display 307 to conserve a constant (or substantially constant) visual angle of the optotype, which reduces the ability for the participant to look down and still see the optotype in their peripheral vision. Additionally, in the embodiment illustrated in FIG. 6, each character (e.g., letter) is shown for approximately 0.25 seconds, the time interval between each character (e.g., each letter) is approximately 0.5 seconds, and the ratio of letter "X"s to other letters or characters is 0.5 in task 410. Additionally, in one or more embodiments, in task 410 may include displaying the letter "X" randomly (or pseudorandomly) among other characters. Furthermore, in one or more embodiments, the characters displayed on the display 307 in task 410 have a color of #5C5C5C and the background on the display 307 has a color of #000000.

In the illustrated embodiment, the method 400 also includes a task 415 of removing the movable barrier 312 and emitting an auditory command or instruction from the speaker 308 for the participant to begin traversing the first and second obstacles 301, 302 positioned in task 405.

In the illustrated embodiment, the method 400 also includes a task 420 of tracking, with the optical motion capture system 305, the foot placement of the participant's feet relative to the obstacles 301, 302 as the participant traverses the obstacles 301, 302.

Figure 7:
FIG. 7 is a schematic representation of a participant's feet during the method of FIG. 5 utilizing the system of FIGS. 4A-4B.

In the illustrated embodiment, the method 400 also includes a task 425 of determining (e.g., calculating or measuring), with the computer 309, the participant's step length while stepping over each of the first and second obstacles 301, 302 and the toe clearance between the toe portion of the participant's foot or shoe while stepping over each of the first and second obstacles 301, 302. In one or more embodiments, the task 425 includes determining, with the optical motion capture system 305 and the computer 309, one or more of the following variables: (i) the walking speed of the participant (e.g., the mean speed of the participant's head in the y-axis); (ii) the vertical toe clearance of the participant's lead foot with respect to the obstacle 301 or 302 (e.g., the vertical distance in the z-axis between the toe of the participant's lead foot and the top of one of the obstacles 301, 302 while crossing the obstacle 301 or 302); (iii) the step width of the participant (e.g., the lateral distance in the x-axis from the heel of the participant's trailing foot before crossing to the heel of the participant's lead foot after crossing one of the obstacles 301, 302); (iv) the step length of the participant (e.g., the anterior-posterior distance in the y-axis from the toe of the participant's trailing foot before crossing to the toe of the participant's lead foot after crossing one of the obstacles 301, 302); (v) the location of the participant's final foot placement before the obstacle 301 or 302 (e.g., the anterior-posterior distance in the y-axis between the toe of the participant's trailing foot and one of the obstacles 301, 302 before crossing the obstacle 301 or 302); (vi) the heel position of the participant's lead foot with respect to the obstacle 301 or 302 (e.g., the anterior-posterior distance in the y-axis between the heel of the participant's lead foot and one of the obstacles 301, 302 after crossing the obstacle 301 or 302); (vii) the toe position of the participant's lead foot with respect to the obstacle 301 or 302 (e.g., the anterior-posterior distance in the y-axis between the toe of the participant's lead foot and one of the obstacles 301 or 302 after crossing the obstacle 301 or 302; (viii) the impact or strike speed of the heel of the participant's lead foot on the floor (e.g., the mean scalar speed (all axis) of the participant's heel strike for the participant's lead foot after crossing one of the obstacles 301 or 302, such as from 10 frames (e.g., 10 frames with a refresh rate of 120 Hz, which is approximately 0.083 seconds ($10*\frac{1}{120}$ second)) before the heel strike to the frame of the heel strike); (ix) the lateral head speed of the participant (e.g., the mean lateral scalar speed in the x-axis of the participant's head between the toe off condition of the participant's lead foot before crossing one of the obstacles 301 or 302 and the heel strike of the participant's trailing foot after crossing the obstacle 301 or 302); (x) the standard deviation (SD) of the participant's lateral head speed (e.g., the standard deviation of the lateral scalar speed in the x-axis of the participant's head for all frames between the toe off condition of the participant's lead foot before crossing one of the obstacles 301 or 301 and the heel strike of the participant's trailing foot after crossing the obstacle 301 or 302); and/or (xi) the margins of stability in the x- and y-axes utilizing a pelvis marker on the participant. FIG. 7 depicts the participant's lead foot and trailing foot during the task of stepping over one of the obstacles 301, 302.

In the illustrated embodiment, the method 400 also includes a task 430 of obtaining or recording the participant's identification (e.g., recall) of one or more specific characters (e.g., one or more specific letters) displayed on the display 307 in task 410. In one or more embodiments, the task 430 may be performed in real-time as the participant traverses the first and second obstacles 301, 302 or after the participant has completed traversing the first and second obstacles 301, 302. For instance, in one or more embodiments, the task 430 includes obtaining the participant's recall of the total number of "X"'s that were displayed on the display 307 in task 410.

The method 400 includes a task 435 of discarding the test results in response to the participant's answers not matching the characters displayed on the display 307 in task 410 or not sufficiently matching the characters displayed on the display 307 in task 410. For instance, in one or more embodiments, the task 435 includes discarding the test results in response to the participant's answers exceeding a threshold error, such incorrectly counting the number of "X"'s displayed on the display 307 by two or more (+/−2 from the actual number of Xs displayed in task 410). The participant's failure to correctly identify the character(s) displayed in task 410 indicates that the participant may have been diverting his or her central visual away from the central vision tasks to assist with the peripheral vision task (e.g., traversing the obstacles 301, 302 positioned in task 405) and therefore the toe clearance and step length results are discarded in task 435 if this condition is not satisfied.

In response to the participant's answers (obtained in task 430) matching the characters displayed on the display 307 in task 410, the method 400 includes a task 440 of recording the test results as valid. In general, a greater toe clearance between the participant's foot and the first and second obstacles 301, 302 and a greater step length while stepping over the first and second obstacles 301, 302 are indicative of cautious walking behavior and therefore greater impairment due to the peripheral optical errors in the participant's vision (i.e., greater toe clearance and greater step length indicate participant's uncertainty in the placement and height of the first and second obstacles 301, 302 and thus greater impairment due to the peripheral optical errors in the participant's vision).

The tasks 405-440 may be repeatedly performed N times (where N is an integer) and one or more characteristics of the first and second obstacles 301, 302 may be varied between subsequent repetitions of tasks 405-440, such as the heights of the first and second obstacles 301, 302, and/or the spacing of the first and second obstacles 301, 302 from the starting line 313. Additionally, in one or more embodiments, the ambient lighting in the room 304 may be varied between subsequent tests. For instance, in one or more embodiments, the ambient lighting in the room 304 may be adjusted between a bright light condition (e.g., 500 lux) and a low light condition (e.g., 1 lux). In one or more embodiments, the ambient lighting in the room 304 may be approximately 14.3 lux. In one or more embodiments, the method 400 may also include a task of emitting an auditory alert (e.g., a beep) from the speaker 308 when the participant has completed traversing the first and second obstacles 301, 302 to signal to the participant to return to the starting line 313 in front of the first obstacle 301 to repeat the test.

While this invention has been described in detail with particular references to exemplary embodiments thereof, the exemplary embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims, and equivalents thereof.

What is claimed is:

1. A method of quantifying an effect of peripheral optical errors on patient locomotion, the method comprising:
projecting, from an overhead video projector, a pattern on a floor in front of a participant, the pattern comprising a plurality of discrete shapes and a plurality of empty spaces between the plurality of discrete shapes;
tracking, with an optical motion capture system, a position of the participant along the pattern as the participant traverses the pattern;
determining foot placement accuracy, utilizing the optical motion capture system and a computer, as the participant walked through the pattern by determining a total area of overlap between the participant's feet and the plurality of empty spaces of the pattern; and
quantifying the effect of the peripheral optical errors on the patient's locomotion based on the foot placement accuracy.

2. The method of claim 1, wherein the projecting the pattern on the floor comprises dynamically revealing portions of the pattern in front of the participant as the participant traverses the pattern.

3. The method of claim 2, further comprising dynamically changing a rate at which the pattern is revealed in front of the participant based on a stride of the participant.

4. The method of claim 2, wherein a length of the portion of the pattern that is dynamically revealed in front of the participant is substantially equal to two strides of the participant.

5. The method of claim 1, wherein the plurality of discrete shapes comprises a plurality of squares.

6. The method of claim 1, further comprising announcing, by a speaker, an instruction for the participant to start walking through the pattern with a left foot first or a right foot first.

7. The method of claim 1, further comprising changing a contrast of the pattern, and repeatedly determining the participant's foot placement accuracy for each different contrast of the pattern.

8. The method of claim 7, further comprising changing ambient lighting, and repeatedly determining the participant's foot placement accuracy for each different illuminance of the ambient lighting.

9. The method of claim 1, further comprising changing a configuration of the pattern, and repeatedly determining the participant's foot placement accuracy for each different configuration of the pattern.

10. The method of claim 9, further comprising conducting a baseline test of the participant's walk without the pattern on the floor to determine the participant's natural stride and walking speed, and wherein the configuration of the pattern is based on the participant's natural stride and walking speed.

11. The method of claim 10, wherein the configuration of the pattern is further based on a shoe size of the participant.

12. A method of quantifying an effect of peripheral optical errors on patient locomotion, the method comprising:
arranging, on a floor, a plurality of obstacles in front of a participant;
intermittently displaying, on a display centered in front of the participant, at least one character;
determining an accuracy of the participant to correctly identify or count each of the at least one character intermittently displayed on the display as the participant traverses the plurality of obstacles;
tracking, with an optical motion capture system, a position of the participant as the participant traverses the plurality of obstacles;
determining, with the optical motion capture system and a computer, a clearance between each of the plurality of obstacles and a foot of the participant as the participant stepped over the plurality of obstacles;
determining, with the optical motion capture system and the computer, a step length of the participant as the participant stepped over the plurality of obstacles; and
quantifying the effect of the peripheral optical errors on the participant's locomotion based on an increase in at least one of the clearance and the step length.

13. The method of claim 12, discarding the effect in response to the participant not identifying or counting each of the at least character displayed on the display within a threshold accuracy.

14. The method of claim 12, further comprising concealing, with a movable barrier, the plurality of obstacles until the participant begins walking.

15. The method of claim 12, wherein the intermittently displaying comprises randomly displaying a particular letter on the display.

16. The method of claim 12, wherein the intermittently displaying the at least one character comprises reducing a size of the at least one character as the participants moves toward the display to maintain a same visual angle of the participant occupied by the at least character.

17. The method of claim 12, further comprising changing a configuration of the plurality of obstacles, and repeatedly determining the clearance and the step length for each different configuration of the plurality of obstacles.

18. The method of claim 12, further comprising changing a location of a least one of the plurality of obstacles, and repeatedly determining the clearance and the step length for each different location of the plurality of obstacles.

* * * * *